United States Patent
Miyamoto (10) Patent No.: US 8,542,794 B2
(45) Date of Patent: Sep. 24, 2013

(54) IMAGE PROCESSING APPARATUS FOR A MOVING IMAGE OF AN OBJECT IRRADIATED WITH RADIATION, METHOD THEREOF, AND STORAGE MEDIUM

(75) Inventor: Hideaki Miyamoto, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 293 days.

(21) Appl. No.: 13/039,493

(22) Filed: Mar. 3, 2011

(65) Prior Publication Data

US 2011/0226956 A1      Sep. 22, 2011

(30) Foreign Application Priority Data

Mar. 16, 2010  (JP) ................................ 2010-059921

(51) Int. Cl.
*G01N 23/04* (2006.01)
(52) U.S. Cl.
USPC ............. 378/62; 378/95; 250/354.1; 382/132
(58) Field of Classification Search
USPC ....... 378/62, 95, 98.11, 98.12; 382/128–132; 250/354.1
See application file for complete search history.

(56) References Cited

U.S. PATENT DOCUMENTS

| 6,055,295 A | 4/2000 | Murthy et al. ................ 378/151 |
| 7,570,792 B2 | 8/2009 | Takahashi ..................... 382/132 |
| 2007/0286527 A1 | 12/2007 | Jabri et al. .................... 382/286 |
| 2008/0025586 A1 | 1/2008 | Baumgart et al. ............ 382/128 |
| 2009/0279663 A1 | 11/2009 | Miyamoto ...................... 378/62 |

FOREIGN PATENT DOCUMENTS

| JP | 2000-010840 | 1/2000 |
| JP | 2003-250789 | 9/2003 |
| JP | 2005-218581 | 8/2005 |

OTHER PUBLICATIONS

Extended European Search Report issued Jun. 30, 2011 in counterpart application 11156339.1.

*Primary Examiner* — Courtney Thomas
(74) *Attorney, Agent, or Firm* — Fitzpatrick, Cella, Harper & Scinto (57) ABSTRACT

A radiation imaging apparatus comprises: an imaging unit to capture a moving image of an object irradiated with radiation; a first extraction unit to extract an object area where an object exists from an exposure field region of radiation in a first frame image of the moving image; a second extraction unit to extract a region of interest as a target for calculation of a first feature amount indicating a feature of an image from a region corresponding to the object area in a second frame image following the first frame image; a first calculation unit to calculate the first feature amount of a region of interest in a third frame image following the second frame image from a region corresponding to the region of interest in the third frame image; and a control unit to control a radiation generating unit based on the first feature amount.

15 Claims, 8 Drawing Sheets

IMAGE PROCESSING APPARATUS FOR A MOVING IMAGE OF AN OBJECT IRRADIATED WITH RADIATION, METHOD THEREOF, AND STORAGE MEDIUM

BACKGROUND OF THE INVENTION

1. Field of the Invention

The present invention relates to a radiation imaging apparatus, radiation imaging method, and storage medium.

2. Description of the Related Art

Recently, with advances in digital technology, digital processing is generally performed on, for example, images obtained by medical X-ray radioscopy. In place of conventional X-ray imaging using films for X-ray diagnosis, a two-dimensional X-ray sensor which can output X-ray images as digital data has also been developed. Digital image processing such as halftone processing is indispensable to a radiation imaging apparatus such as an X-ray radioscopy apparatus using a two-dimensional sensor.

X-ray radioscopy performs radiation exposure control (AEC=Auto Exposure Control) to properly control the amount of X-rays for irradiation by detecting the amount of X-rays transmitted through an object. This radiation exposure control, first of all, acquires feature amounts such as an average value of an X-ray radioscopic image. This X-ray radioscopic image is obtained by X-rays having a pulse-like waveform which are emitted from an X-ray generating unit. This technique then controls X-ray irradiation conditions (for example, the tube voltage, tube current, and X-ray pulse width set for the X-ray generating unit) so as to set a desired exposure based on the comparison between the levels of the feature amounts and reference values.

The purpose of image processing and radiation exposure control in an X-ray radioscopy apparatus is to properly display a region of interest corresponding to an anatomical structure of the human body which is a most important image region in terms of diagnosis.

In image processing and radiation exposure control in an X-ray radioscopy apparatus, a region of interest is extracted from a captured image. Feature amounts used for image processing or radiation exposure control are then calculated from the extracted region of interest. Regions of interest vary depending on imaging target regions and imaging purposes. In radioscopy of the stomach with the use of barium, a region of interest is set on the stomach wall to detect a polyp on the stomach wall. When capturing a moving image of a chest region, a lung field region is set as a region of interest. In cardiac catheterization, a region including the distal end of a catheter and its peripheral region is set as a region of interest.

A region located outside an exposure field when the exposure field is narrowed by a collimator and a so-called direct irradiated region where X-rays directly strike a sensor without passing through an object adversely affect proper region feature calculation. In addition, including a region greatly different in X-ray absorptance from a region of interest, such as a metal piece, in the overall region of interest will adversely affect proper region feature calculation. Such a region therefore should be excluded from the region of interest.

As a conventional method of extracting a region of interest from a given image, there is available threshold processing which sets a threshold for discriminating a region of interest from other regions and extracts a region of interest based on the threshold. In addition, for example, edge extraction processing or the like which extracts the contour shape of an object based on the density distribution shape of an image has been widely used.

For example, Japanese Patent Laid-Open No. 2000-10840 discloses a technique of obtaining the density histogram of an object area in a radiographic image and performing halftone correction processing and dynamic range compression processing for the radiographic image based on the feature amount of the image which is calculated from the density histogram. It is possible to stably extract a feature amount in an object area in an image by extracting image component information corresponding to a bone or soft tissue of an object by using direct irradiated region removal processing and a histogram shape. Even if, for example, the maximum pixel density value in an object area in a radiographic image is smaller than a predetermined pixel density value, this technique allows effective image processing.

In addition, Japanese Patent Laid-Open No. 2005-218581 discloses a technique of extracting an exposure field region for the optimization of image processing parameters. This technique calculates an exposure field candidate region by scoring exposure field likelihoods from a target pixel and its neighboring pixel pattern so as to cope with various collimator shapes such as circular and polygonal shapes. The technique then determines the shape of an exposure field candidate region by obtaining a shape feature amount such as a degree of circularity. The technique extracts an exposure field by an exposure field recognition algorithm specialized to a determined shape. As an algorithm specialized to a determined shape, linear detection processing such as Hough transformation is used for polygonal shapes. Template matching and the like are used for circular shapes. These kinds of processing improve accuracy.

Japanese Patent Laid-Open No. 2003-250789 discloses a technique of extracting a region of interest used for region feature calculation to properly execute at least one of the processes including radiation exposure control and image density conversion in radioscopic imaging that generates images at a relatively low rate of 3 to 5 frames per sec. First, this technique projects (accumulates) image data on an image in the vertical and horizontal directions within a rectangular exposure field region. The technique then generates a one-dimensional array in each direction and executes second derivative computation for the array. The technique then extracts positions at which maximum values are obtained as circumscribed lines (boundary lines) of an exposure field in the respective directions. The technique executes region-of-interest extraction processing for the extracted exposure field region. The technique executes region-of-interest extraction processing by selectively executing an extraction algorithm for each region of interest based on imaging target region information or order (request) information. Region-of-interest extraction techniques include a technique of setting a region of interest as a predetermined region, a technique of detecting a stomach wall (region of interest) as a region around the contour of a barium block, and a technique of detecting a lung field region (region of interest) at the time of capturing a moving image of a chest region. With regards to these techniques, there are disclosed algorithms using image histogram analysis, morphology computation, logical operation using binary images, and the like.

In general, however, an algorithm for extracting a region of interest and calculating a feature amount from the region of interest is complex. It is difficult, especially in an apparatus which processes a large amount of data as in X-ray radioscopic imaging, to accurately extract feature amounts at a required high frame rate (25 fps to 30 fps) in the interval between X-ray irradiation and display. The above conventional techniques are designed to extract feature amounts from images obtained by still image capturing or radioscopic imaging at a relatively low frame rate.

When a conventional technique is applied to radioscopic imaging at a high frame rate, since the feature amount extraction algorithm cannot follow the high frame rate, there is a delay between the start of processing and the calculation of a feature amount. As a result, the information of a frame acquired after the start of feature amount extraction processing is not reflected in an extracted feature amount. This makes it impossible to apply image processing and X-ray control based on an optimal feature amount. Furthermore, when an object makes a large movement, feature amount extraction processing itself sometimes becomes useless. Assume that feature amount extraction processing is started before the movement of an object, and a feature amount is extracted after the movement of the object. In this case, it is impossible to use this feature amount for image processing and X-ray control.

In consideration of the above problem, the present invention provides a radiation imaging apparatus which performs proper feature amount extraction with the information of a new frame being also reflected in radiographic moving image capturing.

SUMMARY OF THE INVENTION

According to one aspect of the present invention, there is provided a radiation imaging apparatus comprising: an imaging unit adapted to capture a moving image of an object irradiated with radiation; a first extraction unit adapted to extract an object area where an object exists from an exposure field region of radiation in a first frame image of the moving image; a second extraction unit adapted to extract a region of interest as a target for calculation of a first feature amount indicating a feature of an image from a region corresponding to the object area in a second frame image following the first frame image; a first calculation unit adapted to calculate the first feature amount of a region of interest in a third frame image following the second frame image from a region corresponding to the region of interest in the third frame image; and a radiation control unit adapted to control a radiation generating unit based on the first feature amount calculated by the first calculation unit.

According to another aspect of the present invention, there is provided a radiation imaging method comprising: capturing a moving image of an object irradiated with radiation; extracting an object area where an object exists from an exposure field region of radiation in a first frame image of the moving image; extracting a region of interest as a target for calculation of a first feature amount indicating a feature of an image from a region corresponding to the object area in a second frame image following the first frame image; calculating the first feature amount of a region of interest in a third frame image following the second frame image from a region corresponding to the region of interest in the third frame image; and controlling a radiation generating unit based on the first feature amount calculated in the calculating the first feature amount.

Further features of the present invention will become apparent from the following description of exemplary embodiments (with reference to the attached drawings).

DESCRIPTION OF THE EMBODIMENTS

An Embodiments of the present invention will now be described in detail with reference to the drawings.

First Embodiment

Figure 1A:
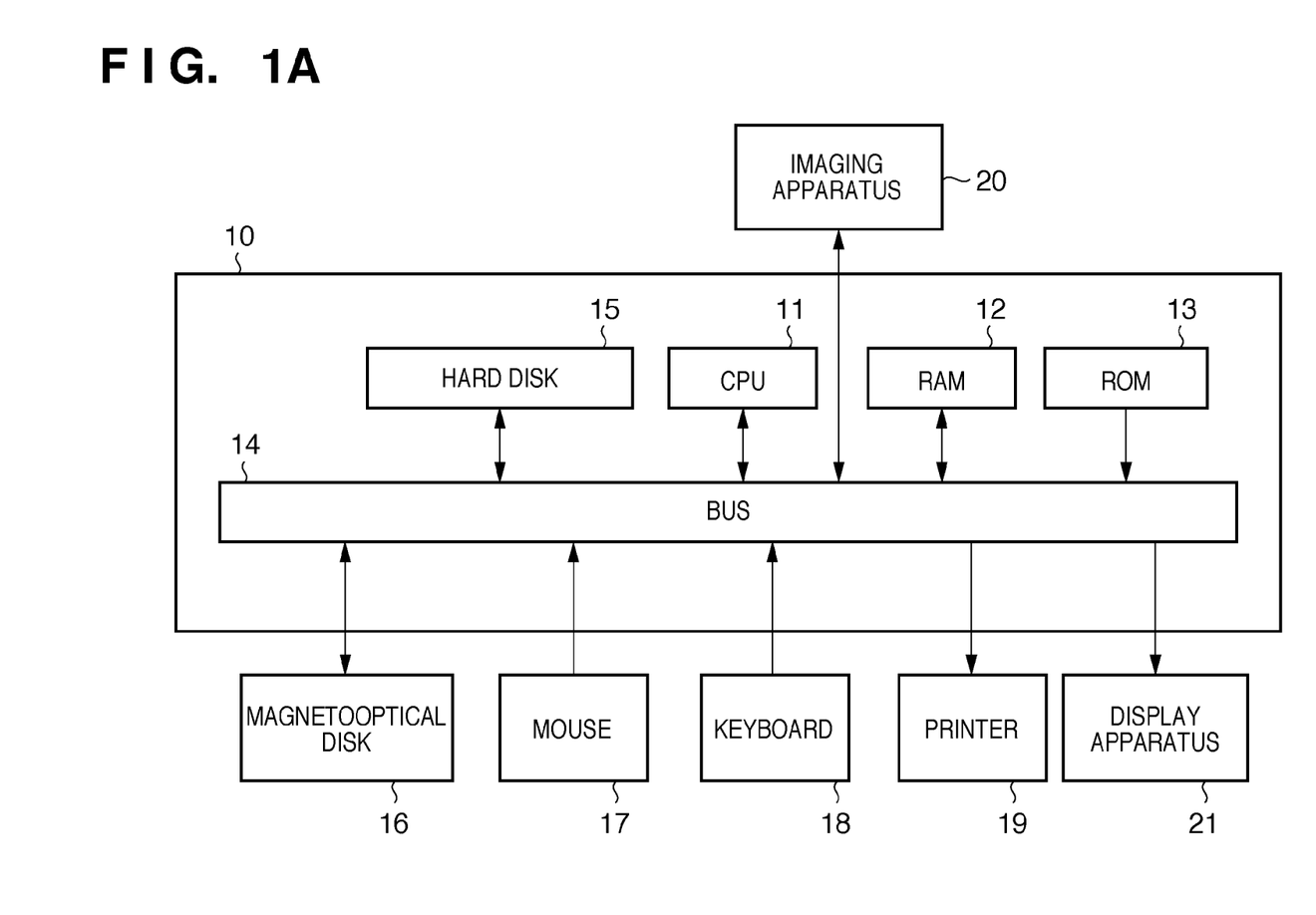
FIG. 1A is a block diagram showing the functional arrangement of a radiation imaging apparatus according to the present invention.

The functional arrangement of a radiation imaging apparatus according to the present invention will be described with reference to FIG. 1A. The radiation imaging apparatus includes a computation apparatus 10 and an imaging apparatus 20. The computation apparatus 10 is connected to the imaging apparatus 20 to allow them to perform data communication with each other.

<Computation Apparatus 10>

A CPU 11 controls the computation apparatus 10 by using the programs and data stored in a RAM 12 and a ROM 13. The CPU 11 can execute computations associated with predetermined image processing by executing a program.

The RAM 12 temporarily stores programs and data loaded from a magnetooptical disk 16 and a hard disk 15. In addition, the RAM 12 temporarily stores image data and the like acquired from the imaging apparatus 20. The RAM 12 is a work area used when the CPU 11 executes various kinds of processes. The ROM 13 stores set data, a boot program, and the like for the computation apparatus 10. A bus 14 connects the respective units in the computation apparatus 10 to allow them to transmit and receive data among them.

The hard disk 15 holds an OS (Operating System) and programs and data by which the CPU 11 causes the respective units shown in FIGS. 1B, 2, 5, and 7 to perform the respective processes. These programs and data are loaded into the RAM 12 under the control of the CPU 11 and are processed by the CPU 11. The hard disk 15 can also store the data of moving images.

The magnetooptical disk 16 is an example of an information storage medium. The magnetooptical disk 16 can store some or all of the programs and data stored in the hard disk 15.

The operator of the computation apparatus 10 operates a mouse 17 and a keyboard 18 to input various kinds of instructions. For example, the operator can set default values in the first embodiment and a predetermined region used for simple image analysis in the second embodiment by using the mouse 17 or the keyboard 18.

Figure 1B:
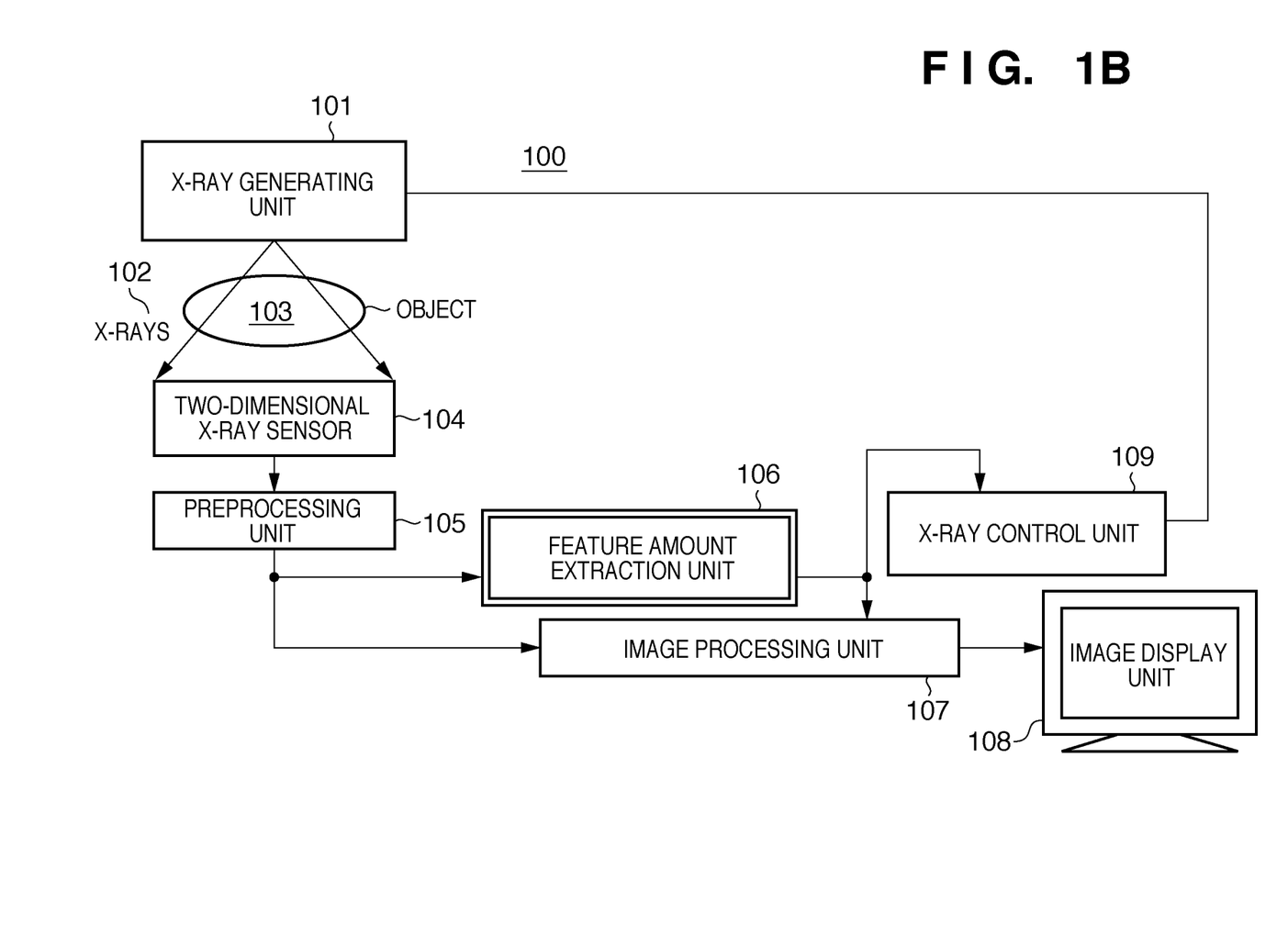
FIG. 1B is a block diagram for explaining the arrangement of a radiation imaging apparatus according to the first embodiment.

A printer 19 prints out an image displayed on an image display unit 108 shown in FIG. 1B onto a printing medium.

A display apparatus 21 includes a CRT or a liquid crystal screen, and can display the processing result obtained by the CPU 11 in the form of images, characters, and the like. For example, the respective units shown in FIG. 1B, 2, 5, or 7 can perform processing to display the image finally output from the image display unit 108. In this case, the image display unit 108 functions as a display control unit for displaying an image on the display apparatus 21.

<Imaging Apparatus 20>

The imaging apparatus 20 can capture a moving image such as that captured by a radiation imaging apparatus (for example, an X-ray radioscopy apparatus). The captured image data is transmitted to the computation apparatus 10. Note that the imaging apparatus 20 may be configured to simultaneously transmit image data regarding a plurality of images to the computation apparatus 10. Alternatively, the imaging apparatus 20 may be configured to sequentially transmit image data every time it performs imaging of a single image. In addition, the computation apparatus 10 transmits X-ray irradiation condition settings for the next frame captured by an X-ray control unit 109 shown in FIGS. 1B and 7 to the imaging apparatus 20. The imaging apparatus 20 updates set imaging conditions based on the received X-ray irradiation conditions for the next frame. Thus the imaging apparatus 20 can capture image data under the updated imaging conditions.

A radiation imaging apparatus (for example, an X-ray radioscopy apparatus 100) according to the first embodiment of the present invention will be described next with reference to FIG. 1B. The X-ray radioscopy apparatus 100 includes an X-ray generating unit 101 (radiation generating unit) which can generate 3 to 30 X-ray pulses per sec and a two-dimensional X-ray sensor 104 which captures a moving image in synchronism with the X-ray pulses of the X-rays 102 transmitted through an object 103. The two-dimensional X-ray sensor 104 functions as an imaging unit to capture a moving image of the object 103 irradiated with X-rays (radiation).

The X-ray radioscopy apparatus 100 includes a preprocessing unit 105 which preprocesses the respective frame images which constitute a moving image output from the two-dimensional X-ray sensor 104 and a feature amount extraction unit 106 which extracts a feature amount from each frame of the preprocessed moving image.

The feature amount extraction unit 106 extracts an object area where an object in an exposure field exists from a frame image as a processing target, and specifies a region of interest upon further removing an X-ray blocking object region (radiation blocking object region). The feature amount extraction unit 106 calculates, as the first feature amount, at least one of the position, size, shape, average luminance value, maximum luminance value, minimum luminance value, barycentric position, luminance value variance, standard deviation, and the like of a region of interest.

The X-ray radioscopy apparatus 100 includes an image processing unit 107 to perform image processing for each frame of a moving image, preprocessed by the preprocessing unit 105, by using the first feature amount calculated by the feature amount extraction unit 106. The image processing unit 107 can perform at least one of halftone conversion processing, sharpening processing, noise suppression processing, and region-of-interest extraction processing as image processing based on the calculated first feature amount.

The X-ray radioscopy apparatus 100 includes the image display unit 108 to display a moving image or the like processed by the image processing unit 107 as an X-ray radioscopic image.

The X-ray radioscopy apparatus 100 also includes the X-ray control unit 109 to perform irradiation condition control at the time of the emission of the next pulse from the X-ray generating unit 101 based on the first feature amount calculated by the feature amount extraction unit 106.

Figure 2:
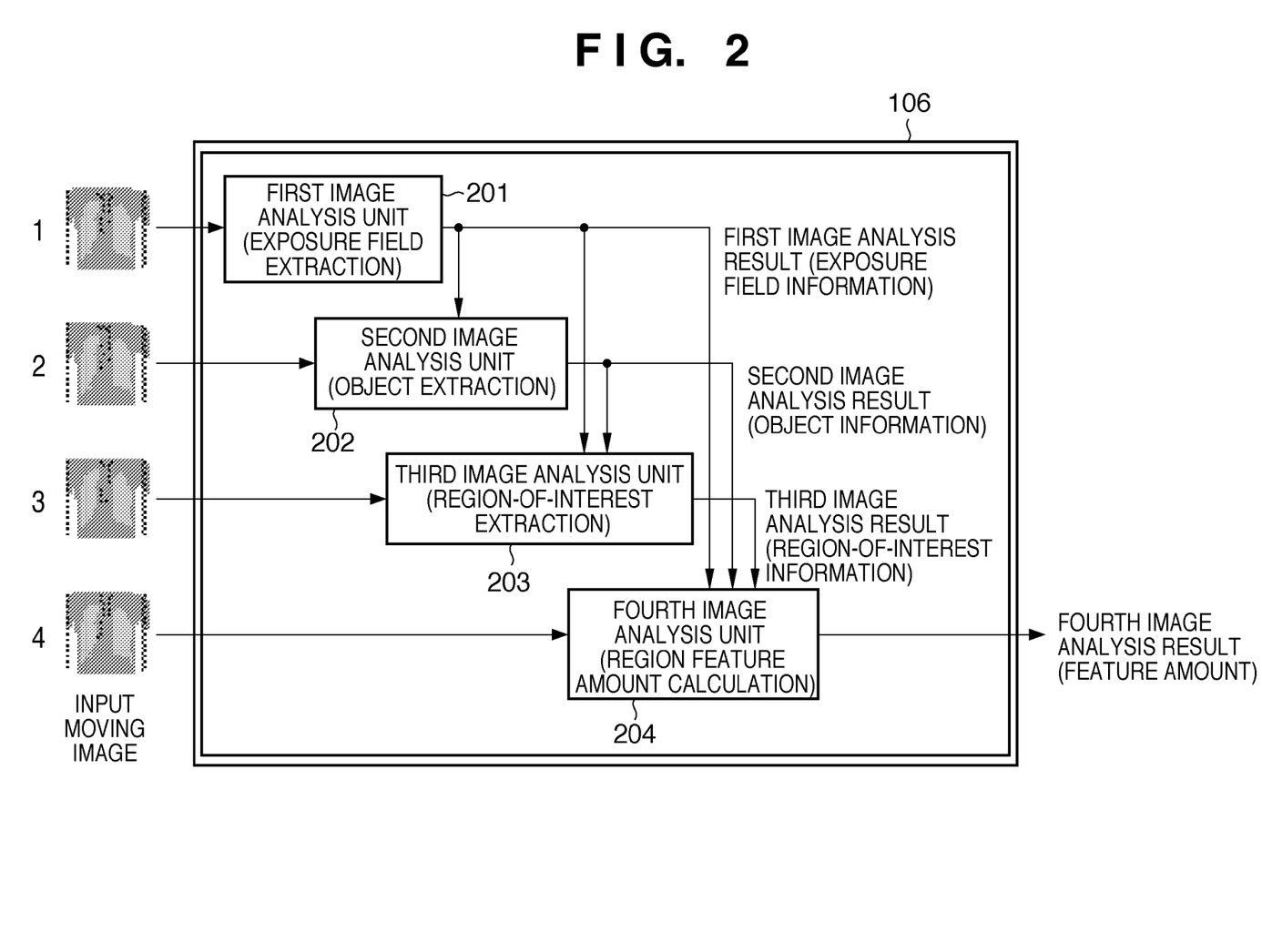
FIG. 2 is a block diagram showing the concrete arrangement of a feature amount extraction unit.

A block diagram showing the detailed arrangement of the feature amount extraction unit 106 will be described with reference to FIG. 2. The feature amount extraction unit 106 includes a first image analysis unit 201, a second image analysis unit 202, a third image analysis unit 203, and a fourth image analysis unit 204.

The first image analysis unit 201 analyzes an image input to the feature amount extraction unit 106 and outputs the first image analysis result (exposure field region) to the second to fourth image analysis units 202 to 204. Note that the first image analysis result output from the first image analysis unit 201 is not used by the third and fourth image analysis units 203 and 204, but is stored to be reconstructed so as to prepare for a case in which a moving image is disturbed by physical swinging or the like. Note that the X-ray radioscopy apparatus may be configured to start from the processing of extracting an object area without extracting an exposure field by the first analysis.

The second image analysis unit 202 functioning as the first extraction unit analyzes an image input to the feature amount extraction unit 106 by using the first image analysis result, and outputs the second image analysis result (object area) to the third and fourth image analysis units 203 and 204. Likewise, the fourth image analysis unit 204 does not use the second image analysis result output from the second image analysis unit 202. It is also possible to extract an object area in the current frame image from the information of an exposure field region extracted from the immediately preceding frame image. Alternatively, it is possible to extract an object area first by analyzing this frame image.

The third image analysis unit 203 functioning as the second extraction unit analyzes an image input to the feature amount extraction unit 106 by using the second image analysis result, and outputs the third image analysis result (a region of interest such as an affected area) to the fourth image analysis unit 204.

The fourth image analysis unit 204 functioning as the first calculation unit analyzes an image input to the feature amount extraction unit 106 by using the third image analysis result, and calculates and outputs the first feature amount as the fourth image analysis result. The fourth image analysis result is the first feature amount supplied as an output from the feature amount extraction unit 106 to the image processing unit 107 and the X-ray control unit 109. The first feature amount will be described in detail later.

An example of an image to be processed by the feature amount extraction unit 106 will be described with reference to FIG. 3. For example, a case in which a chest image 300 is set as an analysis target image will be described.

Figure 3:
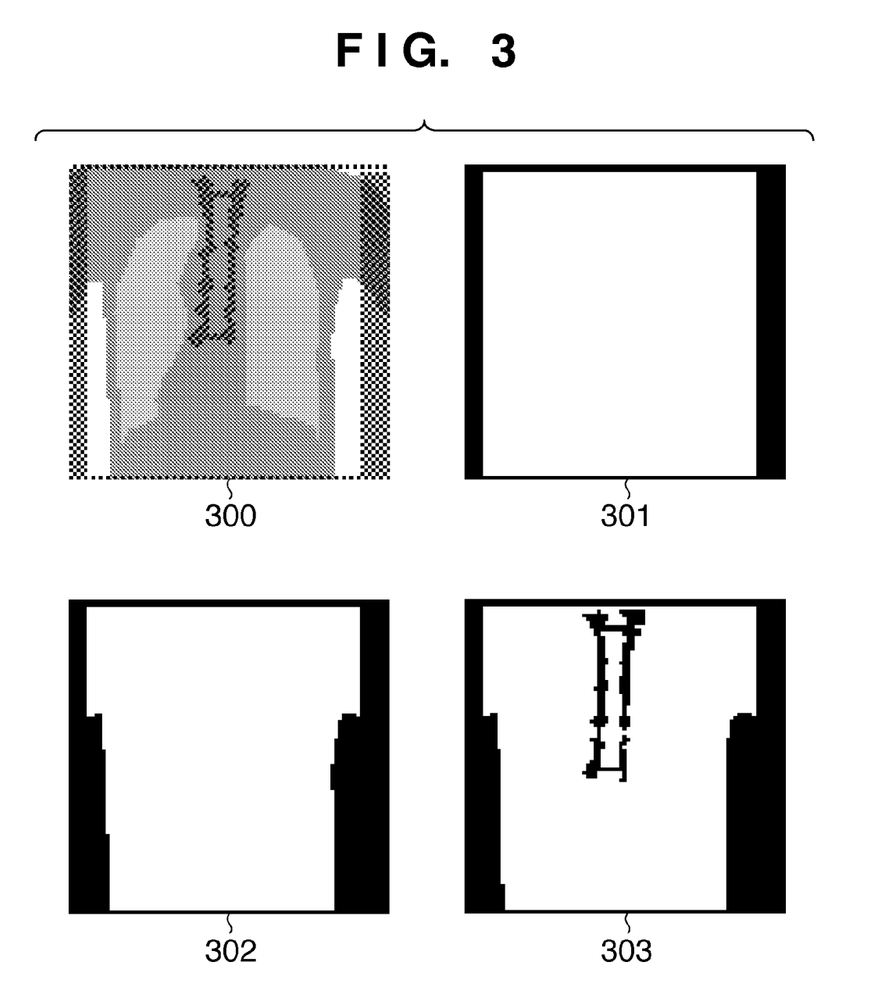
FIG. 3 is a view showing an example of an image as a processing target for the feature amount extraction unit.

Referring to FIG. 3, reference numeral 301 denotes a chart depicting, in black, regions outside an exposure field which are located outside the collimator area narrowed by a collimator (not shown) attached to the X-ray generating unit 101. The region depicted in white is an exposure field region.

Referring to FIG. 3, reference numeral 302 denotes a chart depicting, in black, direct irradiated regions directly irradiated with X-rays which directly strike the two-dimensional X-ray sensor 104 without passing through the object 103 in addition an exposure field region. The region depicted in white is an object area.

Referring to FIG. 3, reference numeral 303 denotes a chart depicting an X-ray blocking object in the object 103 in black in addition to regions outside an exposure field and direct irradiated regions. The region depicted in white is a region of interest.

The following will be referred to as first feature amounts 304 (not shown): the position, size, shape, maximum density value, minimum density value, average density value, variance, standard deviation, and area of a region of interest, the length of a boundary between the region of interest and another region, the moment and center of gravity of the region of interest, and the like which can be calculated.

In this embodiment, the first image analysis unit 201 performs exposure field extraction processing to extract the exposure field region 301. Various methods may be used for this exposure field extraction processing. In general, an exposure field is extracted by using the phenomenon such that a large density change occurs at a boundary between an exposure field region and another region or the contour of an exposure field has a relatively simple shape (linear or circular) depending on the collimator shape. This embodiment also performs exposure field extraction by using the above characteristics of an exposure field region.

In addition, in this embodiment, the second image analysis unit 202 performs object extraction processing to extract the object area 302. Various methods may be used for this object extraction processing. In general, an object area is extracted by using the phenomenon such that a direct irradiated region has a high density value or is in contact with an exposure field region. This embodiment uses the exposure field region 301 extracted by the first image analysis unit 201 to perform the object extraction processing of extracting high-density regions in contact with the exposure field region as direct irradiated regions and extracting the remaining region as the object 103. It is assumed that there is no large change between a given frame image and an immediately succeeding frame. That is, the range of the exposure field region acquired from a given frame image and that of the exposure field acquired from an immediately succeeding frame image correspond to each other and are assumed to be almost common. Therefore, this embodiment considers the range of the exposure field region acquired from a given frame image as that of the exposure field region acquired from an immediately succeeding frame image and extracts an object area from the range. Alternatively, it is possible to extract an object area from a common region where the above ranges fully or partly overlap.

In this embodiment, the third image analysis unit 203 performs the region-of-interest extraction processing of extracting the region of interest 303. This region-of-interest extraction processing is performed by using a general phenomenon that an X-ray blocking object to be removed as a region other than a region of interest has a relatively low density value or has a relatively simple shape (linear) because the object is artificial. This embodiment uses the information of the object area 302 extracted by the second image analysis unit 202 to perform the region-of-interest extraction processing of removing a low-density region or a region having a shape like that of an artificial object as an X-ray blocking object and extracting the remaining region as a region of interest. Likewise, it is assumed that there is no large change between a given frame image and an immediately succeeding frame image. That is, the range of the exposure field region acquired from a given frame image and that of the exposure field acquired from an immediately succeeding frame image correspond to each other and are assumed to be almost the same. Therefore, this embodiment considers the range of the object area acquired from a given frame image as that of the object area acquired from an immediately succeeding frame image, and hence extracts a region of interest from this range. Alternatively, it is possible to extract a region of interest from a common region where the above ranges fully or partly overlap.

Assume that the frame images constituting a moving image will be referred to as the first frame image, the second frame image, the third frame image, and so on, in chronological order, and the first frame image is the first input image. In this case, a given region is extracted from the first frame image. This embodiment then extracts another region from the second frame image based on the extraction result and the second frame image. Likewise, the embodiment extracts still another region from the third frame image based on the extraction result and the third frame image.

In addition, in this embodiment, the fourth image analysis unit 204 performs the region feature calculation processing of extracting the feature amount 304 of the region of interest. In this case, the first feature amount to be extracted depends on the algorithms to be applied to the image processing unit 107 and the X-ray control unit 109 on the subsequent stage. In the embodiment, the image processing unit 107 performs the halftone processing of making the contrast of a region of interest fall within a predetermined range. The image processing unit 107 also extracts the maximum and minimum density values of a region of interest. The X-ray control unit 109 controls X-ray conditions so as to make the average density value of the luminances or the like of the region of interest become constant, and calculates the average density value of the pixels in the region of interest.

Figure 4:
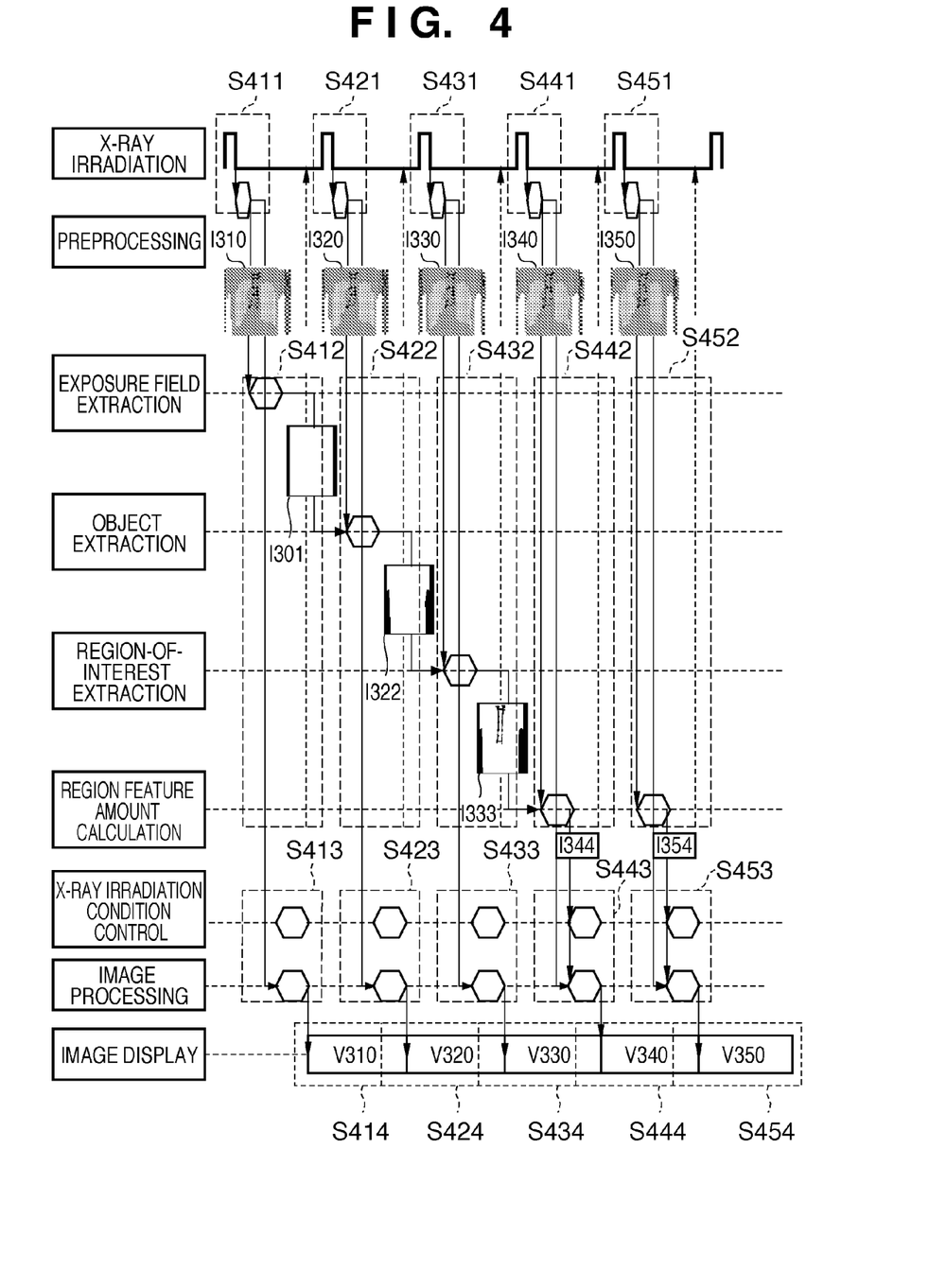
FIG. 4 is a timing chart for explaining a processing procedure according to the first embodiment.

The operation of each unit in this embodiment will be subsequently described with reference to FIG. 4 by exemplifying the first to fourth frames captured by radiographic moving image capturing. For the sake of simplicity, assume that the feature amount extraction unit 106 can execute any one of analyses by the first to fourth image analysis units but cannot execute two or more analyses in the interval from the instant at which the preprocessing unit 105 outputs an image and to the instant at which the image processing unit 107 and the X-ray control unit 109 start operation.

In the subsequent description, reference numeral I3n0 denotes the chest image acquired at the nth frame; I3n1, exposure field region information; I3n2, object area information; I3n3, region-of-interest information; and I3n4, a feature amount. In addition, reference numeral V3n0 denotes a display image obtained by processing the chest image acquired at the nth frame.

In step S411, when the apparatus starts X-ray radioscopy, the X-ray generating unit 101 irradiates the object 103 with the X-rays 102 corresponding to the first pulse. The X-rays 102 are transmitted through the object 103 while being attenuated, and reach the two-dimensional X-ray sensor 104. The two-dimensional X-ray sensor 104 then outputs an X-ray image of the first frame. The preprocessing unit 105 performs preprocessing such as offset correction processing or gain correction processing for the X-ray image output from the two-dimensional X-ray sensor 104. Assume that the image obtained by preprocessing the X-ray image of the first frame is an input image I310 of the first frame to the feature amount extraction unit 106. In step S412, the first image analysis unit 201 of the feature amount extraction unit 106 performs exposure field extraction processing for the input image 310 of the first frame. In this processing, the first image analysis unit 201 extracts exposure field region information I311 and outputs it as the first image analysis result. According to the assumption, the feature amount extraction unit 106 can cause only the first image analysis unit 201 to operate at this time. In step S413, the X-ray radioscopy apparatus 100 causes the image processing unit 107 and the X-ray control unit 109 to operate.

At this time, however, the feature amount extraction unit 106 has not extracted the first feature amounts (the maximum density value, minimum density value, average density value, and the like of the region of interest) to be supplied to the image processing unit 107 and the X-ray control unit 109. Therefore, predetermined default values are given to the image processing unit 107 and the X-ray control unit 109 to perform image processing for the X-ray image I310 of the first frame and X-ray control (radiation control) for the acquisition of an X-ray image of the second frame. In step S414, the image display unit 108 displays the X-ray image (V310) of the first frame having undergone image processing. The apparatus then terminates the processing for the first frame.

In step S421, the X-ray generating unit 101 irradiates the object 103 with the X-rays 102 corresponding to the second pulse. This apparatus executes preprocessing as in step S411, and inputs an input image I320 of the second frame to the feature amount extraction unit 106. In step S422, the feature amount extraction unit 106 causes the second image analysis unit 202 to perform object extraction processing for the input image I320 of the second frame. In this processing, the second image analysis unit 202 extracts object information I322 by using the exposure field region information I311 output in step S412, and outputs the resultant information as the second image analysis result. According to the assumption, the feature amount extraction unit 106 can cause only the second image analysis unit 202 to operate at this time.

In step S423, the X-ray radioscopy apparatus 100 causes the image processing unit 107 and the X-ray control unit 109 to operate. At this time, however, the feature amount extraction unit 106 has not extracted the first feature amounts (the maximum density value, minimum density value, average density value, and the like of the region of interest) to be supplied to the image processing unit 107 and the X-ray control unit 109. Therefore, as in step S413, predetermined default values are given to the image processing unit 107 and the X-ray control unit 109 to perform image processing for the X-ray image I320 of the second frame and X-ray control (radiation control) for the acquisition of an X-ray image of the third frame.

In step S424, the image display unit 108 displays the X-ray image (V320) of the second frame having undergone image processing. The apparatus then terminates the processing for the second frame.

In step S431, the X-ray generating unit 101 irradiates the object 103 with the X-rays 102 corresponding to the third pulse. This apparatus executes preprocessing as in step S411, and inputs an input image I330 of the third frame to the feature amount extraction unit 106.

In step S432, the feature amount extraction unit 106 causes the third image analysis unit 203 to perform region-of-interest extraction processing for the input image I330 of the third frame. In this processing, the feature amount extraction unit 106 extracts X-ray blocking object information by using the object area information I322 output in step S422, and obtains region-of-interest information I333 by removing the X-ray blocking object information from the object area information. The feature amount extraction unit 106 outputs the region-of-interest information I333 as an image analysis result. According to the assumption, at this time, the feature amount extraction unit 106 cannot cause units other than the third image analysis unit 203 to operate.

In step S433, the X-ray radioscopy apparatus 100 causes the image processing unit 107 and the X-ray control unit 109 to operate. At this time, however, the feature amount extraction unit 106 has not extracted the first feature amounts (the maximum density value, minimum density value, average density value, and the like of the region of interest) to be supplied to the image processing unit 107 and the X-ray control unit 109. Therefore, predetermined default values are given to the image processing unit 107 and the X-ray control unit 109 to perform image processing for the X-ray image I330 of the third frame and X-ray control (radiation control) for the acquisition of an X-ray image of the fourth frame. In step S434, the image display unit 108 displays the X-ray image (V330) of the third frame having undergone image processing. The apparatus then terminates the processing for the third frame.

In step S441, the X-ray generating unit 101 irradiates the object 103 with the X-rays 102 corresponding to the fourth pulse. This apparatus executes preprocessing as in step S411, and inputs an input image I340 of the fourth frame to the feature amount extraction unit 106. In step S442, the feature amount extraction unit 106 causes the fourth image analysis unit 204 to perform region feature calculation processing for the input image I340 of the fourth frame. In this processing, the fourth image analysis unit 204 calculates first feature amounts I344 (the maximum density value, minimum density value, average density value, and the like in the region of interest in this embodiment) by using the region-of-interest information I333 output in step S432, and outputs the calculated feature amounts as the fourth image analysis result. The fourth image analysis result (feature amount) is an output from the feature amount extraction unit 106, and is used by the image processing unit 107 and the X-ray control unit 109. According to the assumption, at this time the feature amount extraction unit 106 cannot cause units other than the fourth image analysis unit 204 to operate. In step S443, the X-ray radioscopy apparatus 100 causes the image processing unit 107 and the X-ray control unit 109 to operate. At this time, unlike at the first to third frames, the feature amount extraction unit 106 has extracted the first feature amount I344 to be supplied to the image processing unit 107 and the X-ray control unit 109. Therefore, the feature amount extraction unit 106 supplies the first feature amount I344 to the image processing unit 107 and the X-ray control unit 109 to perform image processing for the X-ray image I340 of the fourth frame and X-ray control (radiation control) for the acquisition of an X-ray image of the fifth frame.

In step S444, the image display unit 108 displays the X-ray image (V340) of the fourth frame having undergone image processing. The apparatus then terminates the processing for the fourth frame.

Subsequently, the feature amount extraction unit 106 performs the same processing as that for the fourth frame in steps S441 to S444 described above until the end of X-ray radioscopy. The feature amount extraction unit 106 extracts the first feature amount I$3n4$ from the input image I$3n0$ of the nth frame by using the region-of-interest information I333, performs image processing and X-ray control, and displays an X-ray image.

This embodiment obtains the following effects in the feature amount extraction processing with a large calculation amount which extracts the first feature amount from a region of interest which is obtained by extracting an exposure field, object, and X-ray blocking object for image processing and X-ray control for the X-ray radioscopy apparatus.

This apparatus divides the processing performed by the feature amount extraction unit into processes to be performed by a plurality of image analysis units. The apparatus then analyzes the latest X-ray image acquired at the operation timing of each image analysis unit. This allows the feature amount extraction unit as a whole to extract the latest information by analyzing a plurality of images.

This makes it possible to acquire information newer than that obtained by analyzing only one X-ray image acquired by the feature amount extraction unit as one unit at the start of operation. That is, it is possible to extract more suitable feature amounts and use them for image processing and X-ray control.

In addition, it is possible to extract necessary feature amounts in real time by selectively executing only minimum image analysis processing (the fourth image analysis unit 204 in this embodiment) after the execution of a series of image analysis processing.

Second Embodiment

Figure 5:
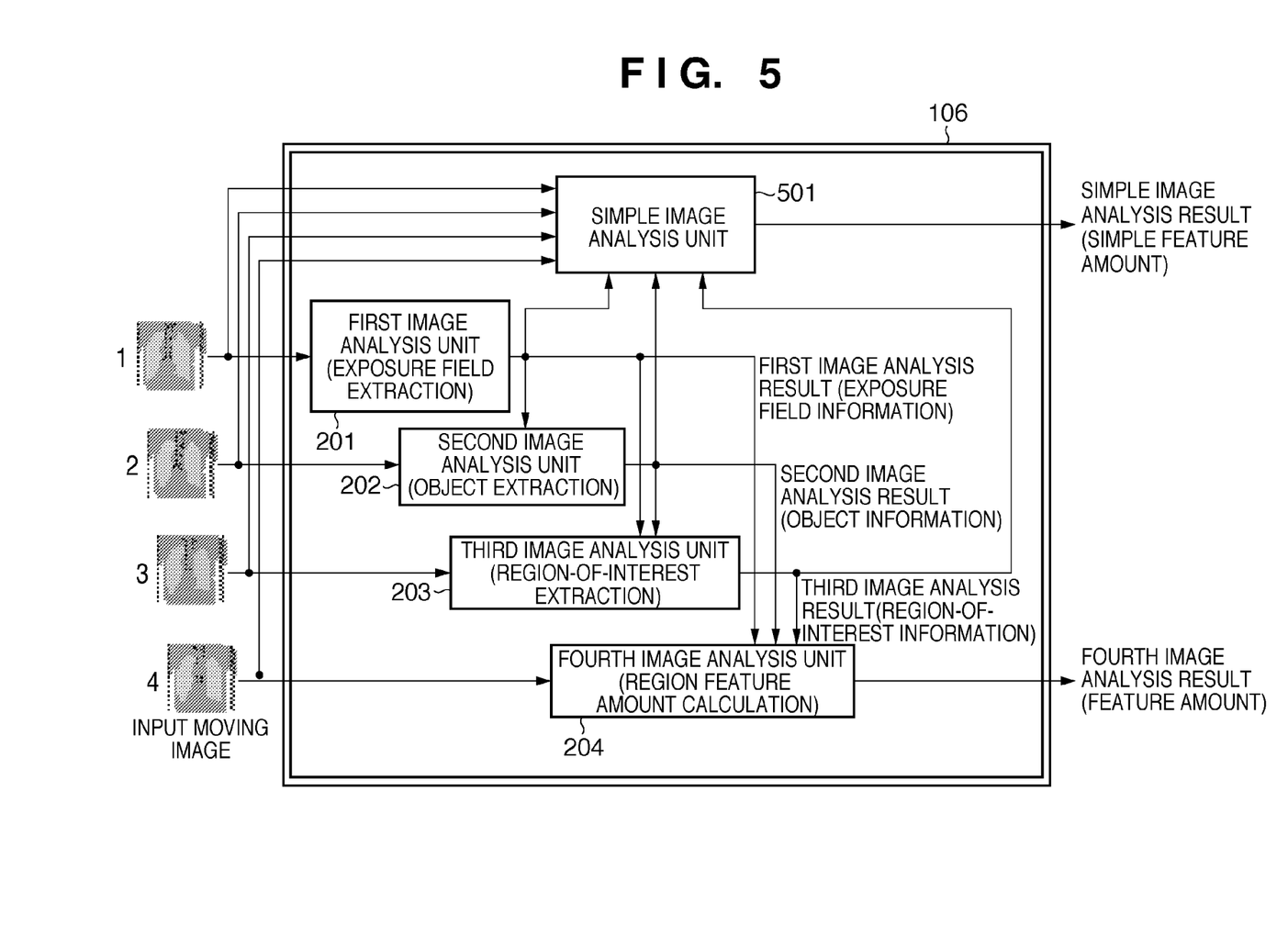
FIG. 5 is a view showing the concrete arrangement of a feature amount extraction unit according to the second embodiment.

A radiation imaging apparatus (for example, an X-ray radioscopy apparatus) according to the second embodiment of the present invention will be described with reference to FIGS. 1B and 5. The contents of an X-ray generating unit 101, X-rays 102, object 103, two-dimensional X-ray sensor 104, preprocessing unit 105, image processing unit 107, image display unit 108, and X-ray control unit 109 in an X-ray radioscopy apparatus 100 in FIG. 1B are the same as those described in the first embodiment. To avoid a redundant description, a description of them will be omitted.

A block diagram showing the detailed arrangement of a feature amount extraction unit 106 according to the second embodiment of the present invention will be described with reference to FIG. 5. The feature amount extraction unit 106 includes a first image analysis unit 201, a second image analysis unit 202, a third image analysis unit 203, a fourth image analysis unit 204, and a simple image analysis unit 501. Referring to FIG. 5, the contents of the first image analysis unit 201, second image analysis unit 202, third image analysis unit 203, and fourth image analysis unit 204 are the same as those described in the first embodiment. To avoid a redundant description, a description of them will be omitted.

The simple image analysis unit 501 functioning as the second calculation unit operates concurrently with the first to fourth image analysis units, and extracts a simple image analysis result from an image input to the feature amount extraction unit 106. A simple image analysis result is a simple feature amount (second feature amount) to be supplied to the image processing unit 107 and the X-ray control unit 109 as an output from the feature amount extraction unit 106.

Simple feature amounts include a maximum luminance value, a minimum luminance value, an average luminance value, a variance, and a standard deviation. The fourth image analysis result output from the fourth image analysis unit is the same feature amount as that described above. The simple image analysis result output from the simple image analysis unit 501 is a feature amount calculated with priority being given to speed rather than accuracy. That is, assume that a simple image analysis result is a simple feature amount guaranteed to be output for each frame, and may be lower in accuracy than the fourth image analysis result. This simple feature amount is used to control irradiation conditions such as an X-ray irradiation range and an irradiation amount, when feature amount calculation processing is not complete. Using such a feature amount can improve the accuracy more than giving predetermined values by default.

In addition, if the first to third image analysis units have output the first to third image analysis results, the simple image analysis unit 501 can improve the accuracy of a simple image analysis result by using these pieces of information, as needed.

In this embodiment, the simple image analysis unit 501 calculates a simple feature amount such as a luminance value from a predetermined designated region or an overlapping portion between the first to third image analysis results and the designated region. Assume that a designated region is a region which is located in the center of an image and has an area 80% of the entire image. A simple feature amount extracted at this time may not be an optimal value but may be a value that presents no serious practical problem. In addition, such a value can be expected to provide stable operation since extraction is guaranteed for each frame.

This embodiment will also exemplify a chest image 300 shown in FIG. 3 as an analysis target image. As in the first embodiment, the first image analysis unit 201 performs exposure field extraction processing, the second image analysis unit 202 performs object extraction processing, the third image analysis unit 203 performs region-of-interest extraction processing, and the fourth image analysis unit 204 performs region feature calculation processing.

Figure 6:
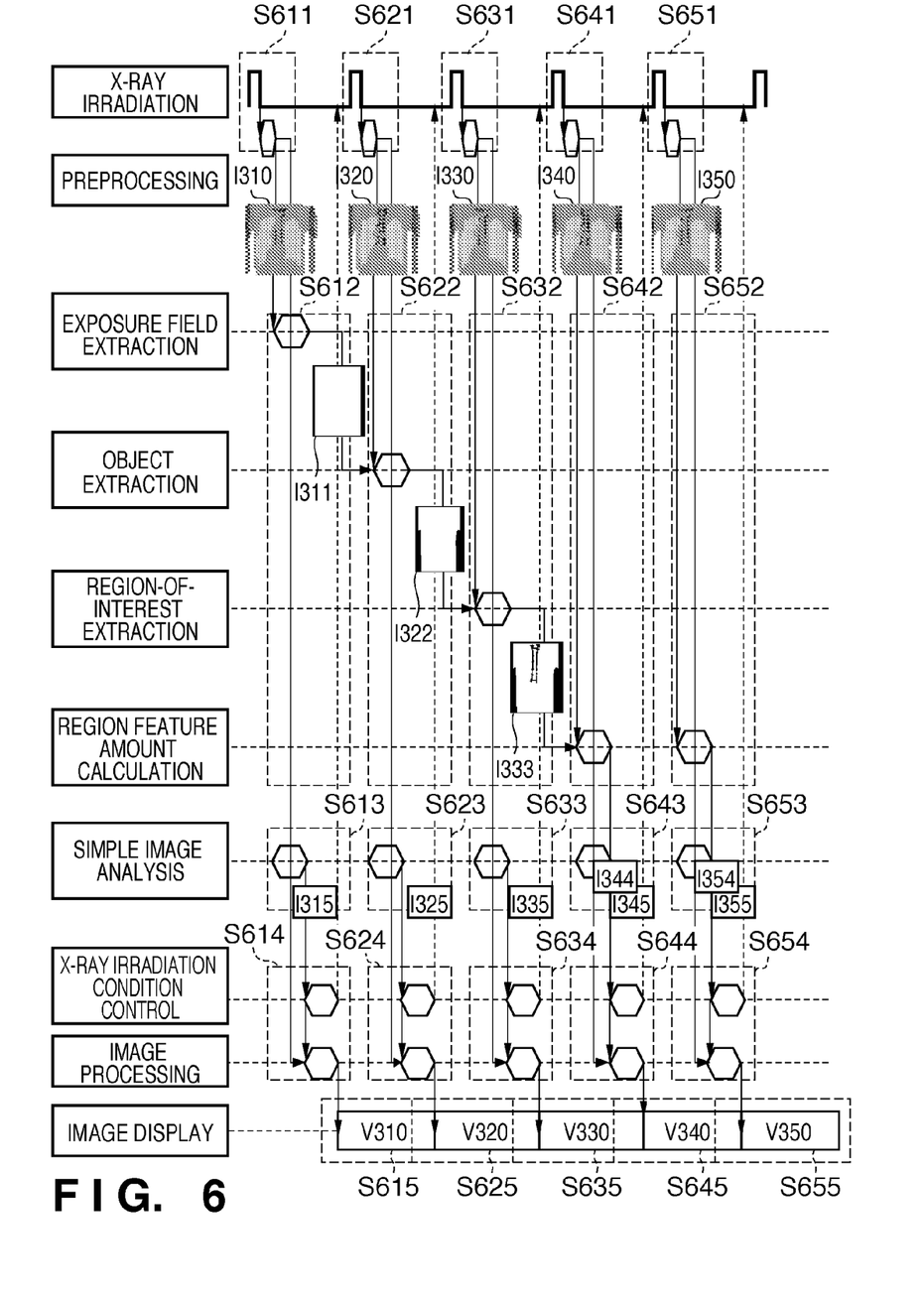
FIG. 6 is a timing chart for explaining a processing procedure according to the second embodiment.

The operation of each unit in this embodiment will be described with reference to FIGS. 3 and 6 by exemplifying the first to fourth frames.

For the sake of simplicity, assume that the feature amount extraction unit 106 can execute any one of the first to fourth image analysis units but cannot execute two or more units in the interval from the instant at which the preprocessing unit 105 outputs an image and to the instant at which the image processing unit 107 and the X-ray control unit 109 start operation.

In the subsequent description, reference numeral I3$n$0 denotes the chest image acquired at the nth frame; I3$n$1, exposure field region information; I3$n$2, object area information; I3$n$3, region-of-interest information; I3$n$4, a feature amount; V3$n$0, a display image; and I3$n$5, a simple image analysis result.

In step S611, the apparatus starts X-ray radioscopy to acquire an input image I310 of the first frame to the feature amount extraction unit 106 by the same processing as that in step S411. In step S612, the feature amount extraction unit 106 causes the first image analysis unit 201 to perform exposure field extraction processing for the input image I310 of the first frame. In this processing, the first image analysis unit 201 extracts exposure field region information I311, and outputs it as the first image analysis result. In step S613, the feature amount extraction unit 106 causes the simple image analysis unit 501 to output a simple image analysis result I315 with respect to the input image I310 of the first frame.

In step S614, the X-ray radioscopy apparatus 100 causes the image processing unit 107 and the X-ray control unit 109 to operate. At this time, however, the feature amount extraction unit 106 has extracted the simple image analysis result I315 as a feature amount to be supplied to the image processing unit 107 and the X-ray control unit 109. Therefore, the apparatus performs image processing for the input image I310 of the first frame and X-ray control to acquire an X-ray image of the second frame by supplying the simple image analysis result I315 to the image processing unit 107 and the X-ray control unit 109. In step S615, the image display unit 108 displays the X-ray image (V310) of the first frame having undergone image processing. The apparatus then terminates the processing for the first frame.

In step S621, the apparatus acquires an input image I320 of the second frame to the feature amount extraction unit 106 by the same processing as that in step S411. In step S622, the feature amount extraction unit 106 causes the second image analysis unit 202 to perform object extraction processing for the input image I320 of the second frame. In this processing, the apparatus extracts the object area information I322 by using the exposure field region information I311 output in step S612, and outputs it as the second image analysis result. In step S623, the feature amount extraction unit 106 causes the simple image analysis unit 501 to output a simple image analysis result I325 with respect to the input image I320 of the second frame. It is possible to improve the accuracy by using the exposure field region information I311 output in step S612. In step S624, the X-ray radioscopy apparatus 100 causes the image processing unit 107 and the X-ray control unit 109 to operate. At this time, however, the feature amount extraction unit 106 has extracted the simple image analysis result I325 as a feature amount to be supplied to the image processing unit 107 and the X-ray control unit 109. Therefore, the apparatus performs image processing for the input image I320 of the second frame and X-ray control to acquire an X-ray image of the third frame by supplying the simple image analysis result I325 to the image processing unit 107 and the X-ray control unit 109. In step S625, the image display unit 108 displays the X-ray image (V320) of the second frame having undergone image processing. The apparatus terminates the processing for the second frame.

In step S631, the apparatus acquires an input image I330 of the third frame to the feature amount extraction unit 106 by the same processing as that in step S411. In step S632, the feature amount extraction unit 106 causes the third image analysis unit 203 to perform region-of-interest extraction processing for the input image I330 of the third frame. In this processing, the apparatus obtains region-of-interest information I333 by extracting X-ray blocking object information by using the object area information I322 output in step S622 and removing it from the object information. The apparatus then outputs the region-of-interest information I333 as the third image analysis result.

In step S633, the feature amount extraction unit 106 causes the simple image analysis unit 501 to output a simple image analysis result I335 with respect to the input image I330 of the third frame. It is also possible to improve the accuracy by using the object area information I322 output in step S622.

In step S634, the X-ray radioscopy apparatus 100 causes the image processing unit 107 and the X-ray control unit 109 to operate. At this time, however, the feature amount extraction unit 106 has extracted the simple image analysis result I335 as a feature amount to be supplied to the image processing unit 107 and the X-ray control unit 109. The apparatus therefore performs image processing for the X-ray image I330 of the third frame and X-ray control to acquire an X-ray image of the fourth frame by supplying the simple image analysis result I335 to the image processing unit 107 and the X-ray control unit 109.

In step S635, the image display unit 108 displays the X-ray image (V330) of the third frame having undergone image processing. The apparatus terminates the processing for the third frame.

In step S641, the apparatus acquires an input image I340 of the fourth frame to the feature amount extraction unit 106 by the same processing as that in step S411. In step S642, the feature amount extraction unit 106 causes the fourth image analysis unit 204 to perform region feature calculation processing for the input image I340 of the fourth frame. In this processing, the apparatus calculates feature amounts I344 (the maximum density value, minimum density value, and average density value in the region of interest in this embodiment) output using the region-of-interest information I333 in step S632, and outputs them as the fourth image analysis result. The fourth image analysis result (feature amounts) is an output from the feature amount extraction unit 106, and is used in the image processing unit 107 and the X-ray control unit 109.

In step S643, the feature amount extraction unit 106 causes the simple image analysis unit 501 to output a simple image analysis result I345 with respect to the input image I340 of the fourth frame. It is also possible to improve the accuracy by using the region-of-interest information I333 output in step S632.

In step S644, the X-ray radioscopy apparatus 100 causes the image processing unit 107 and the X-ray control unit 109 to operate. At this time, unlike in the case with the first to third frames, the feature amount extraction unit 106 has extracted the feature amount I344 to be supplied to the image processing unit 107 and the X-ray control unit 109. Although the simple image analysis result I345 (simple feature amount) is also extracted, the fourth image analysis result I344 including region-of-interest information is generally considered as a more suitable feature amount. The apparatus therefore performs image processing for the input image I340 of the fourth frame and X-ray control for the acquisition of an X-ray image of the fifth frame by supplying the feature amount I344 to the image processing unit 107 and the X-ray control unit 109.

In step S645, the image display unit 108 displays the X-ray image (V340) of the fourth frame having undergone image processing. The apparatus terminates the processing for the fourth frame.

Subsequently, the feature amount extraction unit 106 performs the same processing as that for the fourth frame described with reference to steps S641 to step S645, until the end of X-ray radioscopy. That is, the apparatus extracts the feature amount I3$n$4 using the region-of-interest information I333 for the input image I3$n$0 of the nth frame, and performs image processing, X-ray control, and display of an X-ray image.

The following effect can be obtained from the feature amount extraction processing with a large calculation amount, which extracts a feature amount from a region of interest obtained by extracting an exposure field, object, and X-ray blocking object for image processing and X-ray control for the X-ray radioscopy apparatus.

This embodiment outputs a simple image analysis result for each frame by simple image analysis processing. This makes it possible to stably extract feature amounts, even though they are not optimal, even before the extraction of a region of interest immediately after the start of radioscopy.

Third Embodiment

Figure 7:
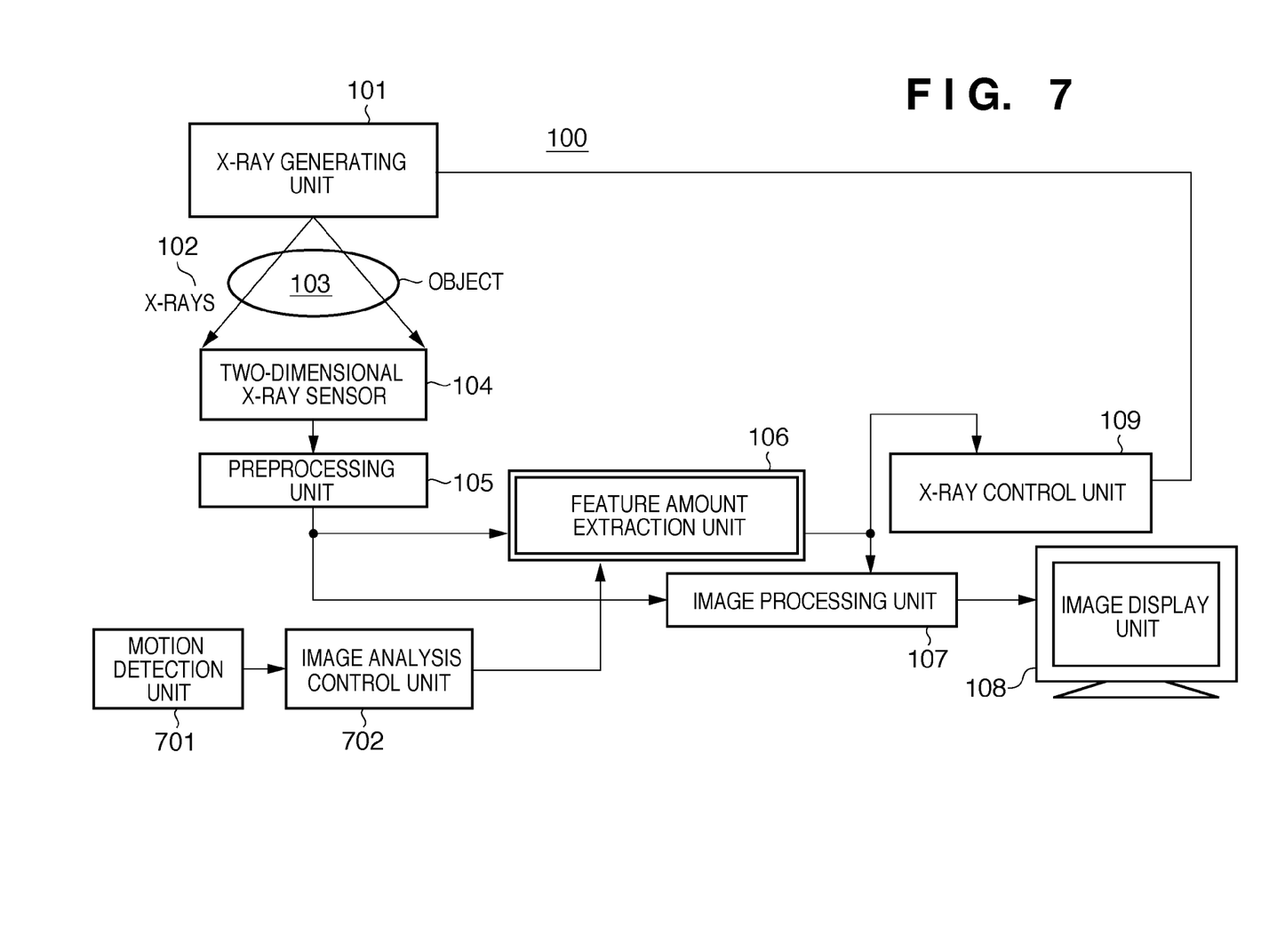
FIG. 7 is a block diagram for explaining the arrangement of an X-ray radioscopy apparatus according to the third embodiment.

A radiation imaging apparatus according to the third embodiment of the present invention will be described with reference to FIG. 7. In the radiation imaging apparatus (for example, the X-ray radioscopy apparatus) in FIG. 7, the contents of an X-ray generating unit 101, X-rays 102, object 103, two-dimensional X-ray sensor 104, preprocessing unit 105, image processing unit 107, image display unit 108, and X-ray control unit 109 are the same as those described in the first embodiment. To avoid a redundant description, a description of them will be omitted. A feature amount extraction unit 106 is the same as that in the second embodiment. To avoid a redundant description, therefore, a description of the feature amount extraction unit will be omitted.

A motion detection unit 701 and an image analysis control unit 702 shown in FIG. 7 constitute an arrangement characteristic to the third embodiment, which will be described in detail below.

The motion detection unit 701 detects a motion in the X-ray radioscopic image captured by the two-dimensional X-ray sensor 104 functioning as an imaging unit. Various motion detection methods are available. There is available a method in which the differences such as luminance value differences between a plurality of frame images constituting a moving image are obtained, the sum total of the difference values is compared with a predetermined threshold, and the occurrence of a motion is determined when the sum total of the difference values becomes larger than a predetermined threshold. This apparatus may be provided with separate sensors which respectively detect the open/close state of the collimator (not shown) attached to the X-ray generating unit 101, the motion of an object, and the mechanical motion of the two-dimensional X-ray sensor. The following description is about a case in which the apparatus uses sensors which respectively detect the motion of the collimator, object, and X-ray sensor.

The image analysis control unit 702 receives detection results from the motion detection unit 701 and controls the operations of first to fourth image analysis units 201 to 204 and a simple image analysis unit 501 (see FIG. 5) which constitute the feature amount extraction unit 106. Assume that the collimator opens or closes, the object moves, or the X-ray sensor moves during feature amount extraction by the first to fourth image analysis units. In this case, an obtained feature amount includes information before the occurrence of the motion, and deterioration in accuracy may have occurred. If, therefore, the motion detection unit 701 detects a motion, the image analysis control unit 702 sets and instructs the feature amount extraction unit 106 to interrupt image analysis processing, resume and restart from the beginning (initialization), and change the order of sequence or discard an image analysis result acquired at this time.

The above arrangement can prevent the use of a feature amount which has deteriorated in accuracy in the subsequent processing. When a given sensor detects motion, the apparatus controls the operation of feature amount extraction processing. This allows early recovery from deterioration in accuracy. Each of the above embodiments has mainly exemplified X-ray radioscopic imaging. It is however possible to apply the contents of the present invention to any types of radiation imaging without being limited to X-ray radioscopic imaging.

According to the present invention, it is possible to extract more suitable feature amounts upon reflection of new frame information in radiation moving image capturing.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-059921, filed Mar. 16, 2010, which is hereby incorporated by reference herein in its entirety.

What is claimed is:

1. An image processing apparatus for a moving image of an object irradiated with radiation, comprising:
   a first extraction unit adapted to extract an object area where an object exists from an exposure field region of radiation in a first frame image of the moving image;
   a second extraction unit adapted to extract a region of interest as a target for calculation of a first feature amount indicating a feature of an image from a region corresponding to the object area in a second frame image following the first frame image; and
   a first calculation unit adapted to calculate the first feature amount of a region of interest in a third frame image following the second frame image from a region corresponding to the region of interest in the third frame image.

2. The apparatus according to claim 1, wherein said first calculation unit calculates, as the first feature amount, at least one of a position, size, shape, average luminance value, maximum luminance value, minimum luminance value, barycentric position, luminance value variance, and standard deviation of the region of interest, based on the region of interest.

3. The apparatus according to claim 1, further comprising:
   a processing unit adapted to perform image processing for a frame image based on the first feature amount calculated by said first calculation unit; and
   a display unit adapted to display a result of image processing performed by said processing unit.

4. The apparatus according to claim 1, further comprising a second calculation unit adapted to calculate a second feature amount indicating a feature of a predetermined region in each frame image constituting a moving image.

5. The apparatus according to claim 4, wherein the second feature amount includes at least one of an average luminance value, maximum luminance value, minimum luminance value, luminance value variance, and standard deviation of the predetermined region.

6. The apparatus according to claim 1, further comprising a detection unit adapted to detect a motion in the moving image,
   wherein, when said detection unit detects a motion in a moving image, said first extraction unit redoes extraction processing of an object area.

7. The apparatus according to claim 6, wherein said detection unit calculates difference values of luminances between a plurality of frame images constituting the moving image, compares a sum total of the difference values with a threshold, and detects occurrence of a motion when the sum total of the difference values is larger than the threshold.

8. The apparatus according to claim 1, further comprising a fourth extraction unit adapted to extract an exposure field region in a frame image preceding the first frame image,
   wherein a region corresponding to the exposure field region extracted by said fourth extraction unit in the first frame image following the frame image is set as an exposure field region of radiation in the first frame image.

9. The apparatus according to claim 8, further comprising a detection unit adapted to detect a motion in the moving image,
   wherein, when said detection unit detects a motion in a moving image, said fourth extraction unit redoes extraction processing of an exposure field region.

10. The apparatus according to claim 9, wherein said detection unit calculates difference values of luminances between a plurality of frame images constituting the moving image, compares a sum total of the difference values with a threshold, and detects occurrence of a motion when the sum total of the difference values is larger than the threshold.

11. The image processing apparatus according to claim 1, further comprising:
a processing unit adapted to perform image processing for a frame image based on the first feature amount calculated by said first calculation unit.

12. The image processing apparatus according to claim 4, further comprising:
a radiation control unit adapted to control a radiation generating unit based on the first feature amount calculated by said first calculation unit,
wherein, when calculation processing for the first feature amount by said first calculation unit is not complete, said radiation control unit controls said radiation generating unit based on the second feature amount calculated by said second calculation unit.

13. A radiographic imaging apparatus comprising:
an imaging unit adapted to capture a moving image of an object irradiated with radiation; and
an image processing apparatus according to claim 1.

14. An image processing method for a moving image of an object irradiated with radiation, comprising:
extracting an object area where an object exists from an exposure field region of radiation in a first frame image of the moving image;
extracting a region of interest as a target for calculation of a first feature amount indicating a feature of an image from a region corresponding to the object area in a second frame image following the first frame image; and
calculating the first feature amount of a region of interest in a third frame image following the second frame image from a region corresponding to the region of interest in the third frame image.

15. A computer-readable non-transitory storage medium storing a computer program for causing a computer to execute each step in a radiation imaging method defined in claim 14.

* * * * *